US010905439B2

(12) United States Patent
Moon et al.

(10) Patent No.: US 10,905,439 B2
(45) Date of Patent: Feb. 2, 2021

(54) SEMICYLINDRICAL OSTEOTOMY DEVICE

(71) Applicant: INJE UNIVERSITY INDUSTRY-ACADEMIC COOPERATION FOUNDATION, Gimhae-si (KR)

(72) Inventors: Sang Won Moon, Busan (KR); Sung Hyuk Moon, Busan (KR)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 88 days.

(21) Appl. No.: 16/321,044

(22) PCT Filed: Aug. 10, 2017

(86) PCT No.: PCT/KR2017/008694
§ 371 (c)(1),
(2) Date: Jan. 28, 2019

(87) PCT Pub. No.: WO2018/030817
PCT Pub. Date: Feb. 15, 2018

(65) Prior Publication Data
US 2019/0167277 A1 Jun. 6, 2019

(30) Foreign Application Priority Data
Aug. 10, 2016 (KR) .................. 10-2016-0101764

(51) Int. Cl.
*A61B 17/16* (2006.01)
*A61B 17/14* (2006.01)
(Continued)

(52) U.S. Cl.
CPC ........ *A61B 17/1637* (2013.01); *A61B 17/149* (2016.11); *A61B 17/151* (2013.01);
(Continued)

(58) Field of Classification Search
CPC ..... A61B 17/149; A61B 17/15; A61B 17/157; A61B 17/1626; A61B 17/1628; A61B 17/1637; A61B 17/1662
See application file for complete search history.

(56) References Cited

U.S. PATENT DOCUMENTS 1,543,195 A * 6/1925 Thygesen ................ A61D 1/10
606/176
3,495,590 A * 2/1970 Zeiller .................... A61F 15/02
602/9
(Continued)

FOREIGN PATENT DOCUMENTS

CN 101361670 A 2/2009
CN 204049751 U 12/2014
(Continued)

OTHER PUBLICATIONS

International Search Report for PCT/KR2017/008694 dated Sep. 22, 2017 from Korean Intellectual Property Office.

*Primary Examiner* — Anu Ramana
(74) *Attorney, Agent, or Firm* — Revolution IP, PLLC

(57) ABSTRACT

Provided is a semi-cylindrical osteotomy device including: a guide portion where a tibia accommodating space in which a tibia is accommodated is formed; a cutter portion moving in the tibia accommodating space and cutting the tibia while moving along an inner circumferential surface of the guide portion; and a driving unit driving the cutter portion. According to the semi-cylindrical osteotomy device, stability of a surgery is increased by inserting the guide portion by approaching a side surface of the tibia to minimize an exposed portion of a bone. Also, a wire saw moves along a slit of the guide portion, and thus a cut bone surface of a semi-cylindrical shape is easily and quickly formed.

8 Claims, 4 Drawing Sheets

(51) Int. Cl.
*A61B 17/15* (2006.01)
*A61B 17/17* (2006.01)

(52) U.S. Cl.
CPC ...... *A61B 17/1626* (2013.01); *A61B 17/1628* (2013.01); *A61B 17/1662* (2013.01); *A61B 17/1739* (2013.01)

(56) References Cited

U.S. PATENT DOCUMENTS

| | | | |
|---|---|---|---|
| 3,835,859 A * | 9/1974 | Roberts | A61B 17/32056 606/79 |
| 3,999,294 A * | 12/1976 | Shoben | B23D 57/023 30/166.3 |
| 5,725,530 A * | 3/1998 | Popken | A61B 17/15 30/166.3 |
| 5,849,023 A * | 12/1998 | Mericle | A61B 17/1628 606/180 |
| 6,190,390 B1 | 2/2001 | McAllister | |
| 7,189,240 B1 * | 3/2007 | Dekel | A61B 17/1671 606/84 |
| 7,738,969 B2 * | 6/2010 | Bleich | A61B 17/1671 600/373 |
| 8,021,379 B2 * | 9/2011 | Thompson | A61B 17/320758 606/128 |
| 8,062,300 B2 * | 11/2011 | Schmitz | A61B 17/1659 606/85 |
| 2007/0083209 A1 | 4/2007 | Schenberger | |
| 2014/0378977 A1 | 12/2014 | Russi | |

FOREIGN PATENT DOCUMENTS

| | | |
|---|---|---|
| CN | 104546112 A | 4/2015 |
| KR | 20-0382862 Y1 | 4/2005 |
| WO | 2007-041027 A2 | 4/2007 |

\* cited by examiner (a) (b) (c)

SEMICYLINDRICAL OSTEOTOMY DEVICE

TECHNICAL FIELD

The present disclosure relates to an osteotomy device, and more particularly, to a semi-cylindrical osteotomy device for cutting a tibia to a semi-cylindrical shape to rearrange the tibia.

BACKGROUND ART

Among the commonly occurred damage to knee joints, degenerative arthritis of knees requiring surgical treatment is increasing in young and active ages. Since the above-mentioned degenerative arthritis is accompanied by varus deformity, the frequency of surgeries using osteotomy which preserves and treats the joints is increasing.

The above-mentioned osteotomy is a method of cutting a bone and re-aligning an angle and position of the bone, and is able to improve a joint function by correcting deformation of the bone, alleviate the pain of a knee joint by correcting an abnormal axis of a lower limb, and improve functions of a joint.

Generally, a method for osteotomy includes open osteotomy and closed osteotomy. In the open osteotomy, an inner side of a tibia is cut to cut an upper portion of the tibia, and then a cut portion is wedged to a desired size and fixed with a metal plate. The tibia may be rearranged by performing a bone graft on the wedge-shaped space.

In the closed osteotomy, a proximal tibiofibular joint is divided or a fibula is cut by cutting an outer portion of a tibia, thereby removing a bone of a desired size from an upper portion of the tibia in a wedge shape. The tibia may be rearranged by correcting an angle of the tibia removed in the wedge shape and then fixing upper and lower bones together with a metal plate.

However, in the open osteotomy and the closed osteotomy described above, a bone is cut into a wedge shape to graft the bone in a space of the wedge shape or a bone is removed to realign a tibia, and thus the length of tibia is changed and an interaction of the tibia with an adjacent fibula or patella is adversely affected.

Thus, in order to improve demerits of the open osteotomy and the closed osteotomy described above, a semi-cylindrical osteotomy has been developed in which an anterior portion of a tibia is cut to cut an upper portion of the tibia in a semi-cylindrical shape. The semi-cylindrical osteotomy allows the tibia to be rearranged by cutting the tibia into the semi-cylindrical shape and then aligning the tibia as desired along a cut bone surface of the tibia that is curvedly bent.

A device for a conventional semi-cylindrical osteotomy as described above is disclosed in KR Registered Utility Model No. 20-0382862.

However, the device of the conventional semi-cylindrical osteotomy has a high risk of surgery because an exposed portion of a bone is increased by cutting an anterior portion of a tibia to cut the tibia in a semi-cylindrical shape.

DESCRIPTION OF EMBODIMENTS

Technical Problem

The present disclosure is designed to solve the problems of the related art, and therefore the present disclosure is directed to providing a semi-cylindrical osteotomy device enabling a stable medical procedure by minimizing an exposed portion of a bone.

Solution to Problem

According to an aspect of the present disclosure, a semi-cylindrical osteotomy device includes: a guide portion where a tibia accommodating space in which a tibia is accommodated is formed; a cutter portion moving in the tibia accommodating space and cutting the tibia while moving along an inner circumferential surface of the guide portion; and a driving unit driving the cutter portion.

The guide portion may include a center portion curvedly formed.

The cutter portion may move along the inner circumferential surface of the guide portion to cut the tibia in a curved surface.

The guide portion may include: a pipe where an internal space is formed to accommodate the cutter portion, and arranged along an outer circumference of the tibia; and a slit formed along an inner circumference of the pipe.

The cutter portion may be configured in a wire saw, may be arranged along the outer circumference of the tibia by being provided along an internal space of the guide portion, and may cut the tibia in a curved surface by moving through the slit.

The guide portion may include: an anterior guide pipe arranged at an anterior portion of the tibia, including a center portion forming a semi-circular shape by being curved, and including an anterior slit along a length direction at a side contacting the tibia; a posterior guide pipe arranged at a posterior portion of the tibia, including a center portion forming a semi-circular shape by being curved, and including a posterior slit along a length direction at a side contacting the tibia; and a connecting unit provided at one ends of the anterior guide pipe and posterior guide pipe to connect the anterior guide pipe and the posterior guide pipe.

The cutter portion may be configured in a wire saw, may be arranged along the outer circumference of the tibia by being provided along inner spaces of the anterior guide pipe and posterior guide pipe, and may cut the tibia in a curved surface by moving along the anterior slit and the posterior slit from other ends to the one ends of the anterior guide pipe and posterior guide pipe.

The driving unit may include: a rotating shaft where both ends of the wire saw are fixed and wound around; a driving motor controlling the rotating shaft; and a controller controlling the driving motor.

The driving unit may include: a body provided at one side of the guide portion and where a space is formed; and a moving body to which both ends of the wire saw are fixed and slidably moves by being provided inside the body.

Advantageous Effects of Disclosure

According to a semi-cylindrical osteotomy device according to the present disclosure, stability of a surgery is increased by inserting a guide portion to a side surface of a tibia to minimize an exposed portion of a bone.

Also, a wire saw moves along a slit of the guide portion, and thus a cut bone surface of a semi-cylindrical shape may be easily and quickly formed.

BEST MODE

Hereinafter, the present disclosure will be described more fully with reference to the accompanying drawings, in which exemplary embodiments of the disclosure are shown. The terms or words used herein must not be interpreted in their common or dictionary definitions, but must be interpreted in the meanings and concept corresponding to the aspect of the present disclosure, based on the principle that the inventor(s) can suitably define the concept of terms in order to describe the disclosure in the best manner.

Accordingly, the embodiments and drawings described herein are only preferred examples, and do not represent the technical aspects of the present disclosure. Thus, one of ordinary skill in the art understands that the disclosure may be embodied in many different forms.

Hereinafter, exemplary embodiments of the present disclosure will be described in detail with reference to accompanying drawings.

Figure 1:
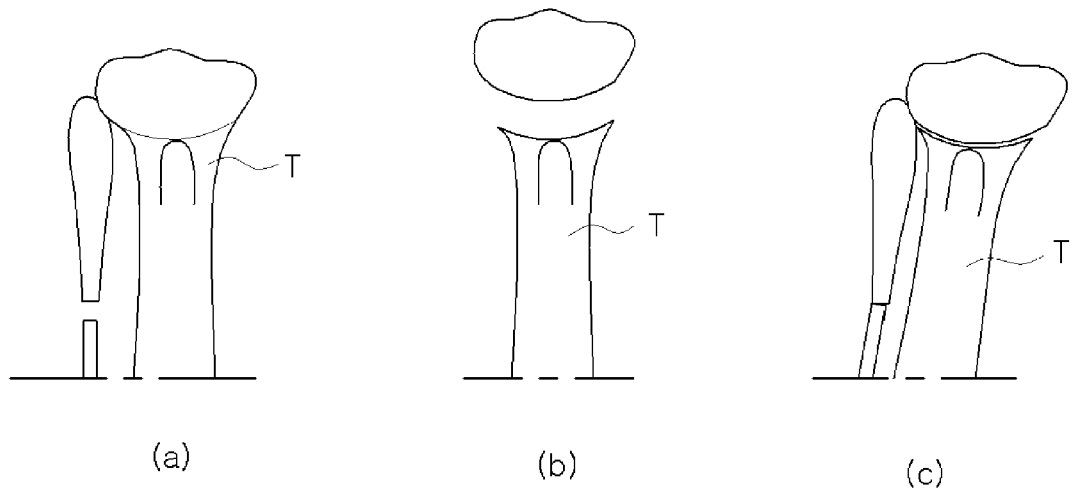
FIG. 1 is front views showing stepwise processes of semi-cylindrical osteotomy.
Figure 2:
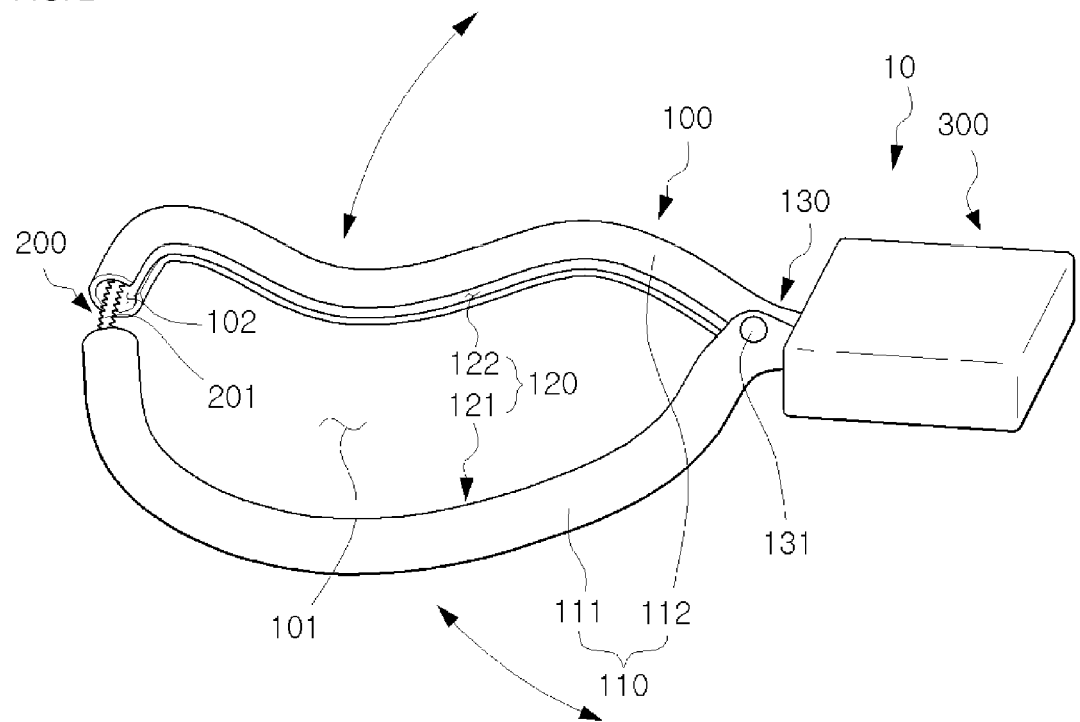
FIG. 2 is a perspective view of a semi-cylindrical osteotomy device according to an embodiment of the present disclosure.
Figure 3:
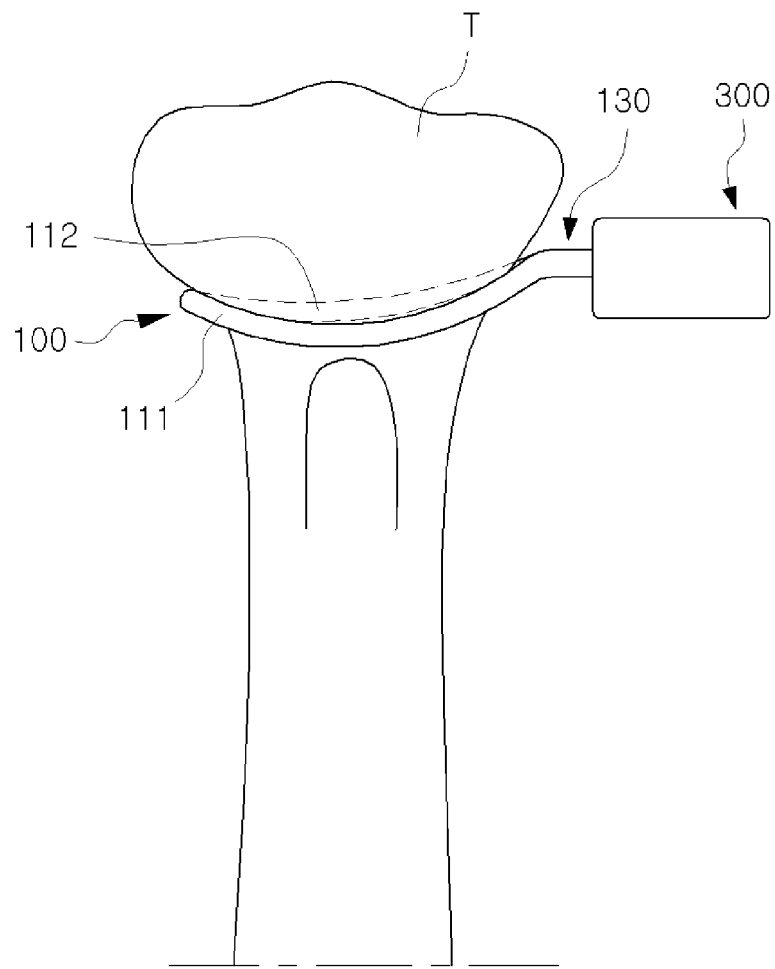
FIG. 3 is a front view of the semi-cylindrical osteotomy device of FIG. 2.
Figure 4:
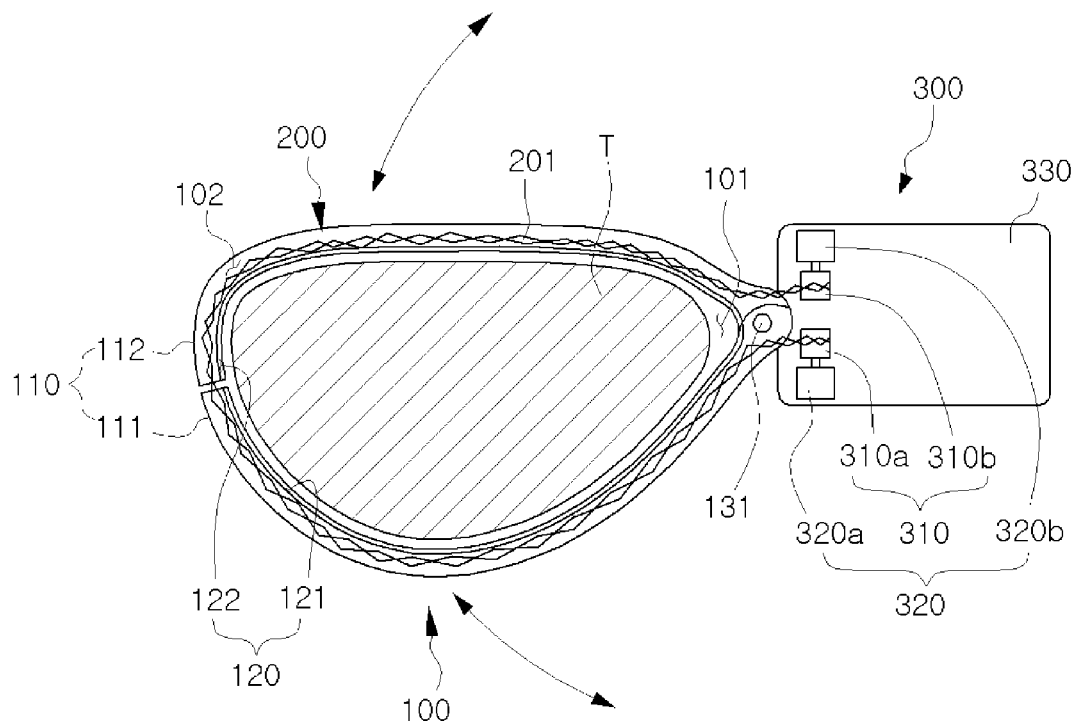
FIG. 4 is a cross-sectional view of the semi-cylindrical osteotomy device of FIG. 2 cut along a guide portion.
Figure 5:
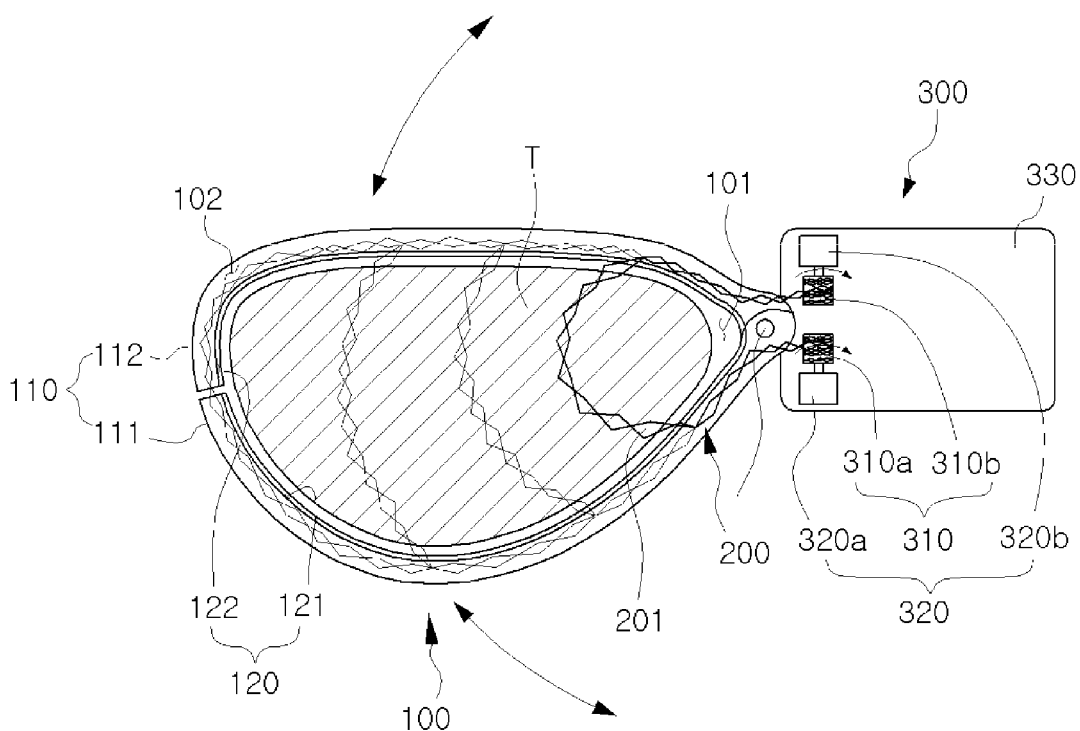
FIG. 5 is a cross-sectional view showing a state of use of the semi-cylindrical osteotomy device of FIG. 2 cut along the guide portion.

First, stepwise processes of semi-cylindrical osteotomy will be described with reference to FIG. 1. FIG. 1(a) illustrates a tibia T that needs to be rearranged. Semi-cylindrical osteotomy cuts an upper portion of the tibia that needs to be rearranged in a semi-cylindrical shape as shown in FIG. 1(b). Then, as shown in FIG. 1(c), the tibia T is rearranged and corrected as desired based on a goal of a subject of the osteotomy, and then is fixed by using a metal plate. Accordingly, the tibia may be rearranged and corrected without having to remove or insert a bone.

Referring to FIGS. 2 through 6, a semi-cylindrical osteotomy device 10 of the present disclosure is for performing the above-described semi-cylindrical osteotomy, and includes a guide portion 100, a cutter portion 200, and a driving unit 300.

The guide portion 100 is a guiding configuration for cutting an upper portion of the tibia T in a semi-cylindrical shape, and includes a tibia accommodating space 101 in which the tibia T is accommodated. In detail, the guide portion 100 may have a center portion curvedly formed to cut the upper portion of the tibia T in a semi-cylindrical shape. The guide portion 100 may include a pipe 110 and a slit 120.

The pipe 110 is a pipe having an internal space 102, wherein the cutter portion 220 described later may be accommodated in the internal space 102. Also, the pipe 110 may be arranged along an outer circumference of the tibia T such that the tibia T may be arranged in the tibia accommodating space 101 formed along an inner circumference of the pipe 110.

The slit 120 is formed along the inner circumference of the pipe 110, and is formed at a side contacting the tibia T. In other words, the slit 120 is formed along a shape of the pipe 110, and the cutter portion 200 may cut the tibia T in a curved surface by moving along the slit 120.

In addition, the pipe 110 may include an anterior guide pipe 111 and a posterior guide pipe 112, and the slit 120 may include an anterior slit 121 and a posterior slit 122.

The anterior guide pipe 111 is a pipe arranged at an anterior portion of the tibia T and including the internal space 102. Also, the anterior guide pipe 111 is formed such that a center portion is curved to form a semi-circular shape, and thus the cutter portion 200 may cut the tibia T in a semi-circular shape by moving along the anterior guide pipe 111. The anterior guide pipe 111 may include the anterior slit 121 along a length direction at a side contacting the tibia T. In other words, the anterior slit 121 is formed such that a center portion is curved to form a semi-circular shape along the anterior guide pipe 111.

The posterior guide pipe 112 is a pipe arranged at a posterior portion of the tibia T and including the internal space 102. Also, the posterior guide pipe 112 is formed such that a center portion is curved to form a semi-circular shape, and thus the cutter portion 220 may cut the tibia T in a semi-circular shape by moving along the posterior guide pipe 112. The anterior guide pipe 111 may include the posterior slit 122 along a length direction at a side contacting the tibia T. In other words, the posterior slit 122 is formed such that a center portion is curved to form a semi-circular shape along the posterior guide pipe 112.

Meanwhile, the guide portion 100 may include a connecting unit 130 provided at one ends of the anterior guide pipe 111 and the posterior guide pipe 112. The connecting unit 130 connects the anterior guide pipe 111 and the posterior guide pipe 112, and the anterior guide pipe 111 and the posterior guide pipe 112 may be stably supported by the connecting unit 130 respectively at the anterior portion and the posterior portion of the tibia T. Also, the connecting unit 130 may be combined to the anterior guide pipe 111 and the posterior guide pipe 112 via a hinge 131. The anterior guide pipe 111 and the posterior guide pipe 112 may be arranged on the outer circumference of the tibia T by rotating based on the hinge 131. The connecting unit 130 may be configured in the hinge 131 such that the anterior guide pipe 111 and the posterior guide pipe 112 are rotatable based on the hinge 131, but is not limited thereto, and the connecting unit 130 may be configured in a flexible material, an elastic material, or the like such that other ends of the anterior guide pipe 111 and posterior guide pipe 112 are easily spread in both sides based on the connecting unit 130. Accordingly, the guide portion 100 may be easily arranged on the outer circumference of the tibia T.

The cutter portion 200 is for cutting the tibia T, and moves in the tibia accommodating space 101. In other words, the cutter portion 200 traverses the tibia accommodating space 101 along an inner circumferential surface of the guide portion 100 to cut the tibia T in a curved surface.

In detail, the cutter portion 200 may be configured in a wire saw 201. The wire saw 201 may be provided along the internal space 102 of the pipe 110. Accordingly, the wire saw 201 may stably move along the internal space 102, and arranged along the outer circumference of the tibia T. The wire saw 201 arranged along the outer circumference of the tibia T cuts the tibia T in the curved surface by moving to the tibia accommodating space 102 through the slit 120.

In other words, the wire saw 201 is arranged along the outer circumference of the tibia T by being provided along the internal spaces 102 of the anterior guide pipe 111 and posterior guide pipe 112. The wire saw 201 may cut the tibia T in the curved surface by moving along the anterior slit 121 and the posterior slit 122 whose center portions are curved to form a semi-circular shape. Also, the wire saw 201 may cut the tibia T by moving from other ends to the one ends of the anterior guide pipe 111 and posterior guide pipe 112 to traverse the tibia accommodating space 101. When the wire saw 201 is configured to cut the tibia T by moving from the other ends to the one ends of the anterior guide pipe 111 and posterior guide pipe 112, the number of times of traversing a cut portion of the tibia T is minimized, and thus stability and efficiency are increased.

The driving unit 300 is for driving the cutter portion 200, and may include a rotating shaft 310, a driving motor 320 and a controller 330.

Both ends of the wire saw 201 are fixed and wound around the rotating shaft 310. In other words, the rotating shaft 310 is formed in a cylindrical shape, and the both ends of the wire saw 201 are wound when the both ends of the wire saw 201 are fixed and rotated on an outer circumference of the cylindrical shape. Accordingly, because the wire saw 201 is wound around the rotating shaft 310, the wire saw 201 may cut the tibia T by moving from the other ends to the one ends of the anterior guide pipe 111 and posterior guide pipe 112. In addition, the rotating shaft 310 may be configured in a pair such that the both ends of the wire saw 201 are respectively wound. In other words, the rotating shaft 310 may include a first rotating shaft 310a where one end of the wire saw 201 is wound and a second rotating shaft 310b where the other end of the wire saw 201 is wound. Also, the first rotating shaft 310a and the second rotating shaft 310b may repeatedly alternately rotate to induce sawing of the wire saw 201, thereby cutting the tibia T.

The driving motor 320 drives the rotating shaft 310. The driving motor 320 provides driving power such that the rotating shaft 310 rotates. The driving motor 320 may include a first driving motor 320a rotating the first rotating shaft 310a and a second driving motor 320b rotating the second rotating shaft 310b. The tibia T may be efficiency cut via the driving motor 320.

The controller 330 controls a rotating speed, a number of revolution, etc. of the driving motor 320. In other words, the controller 330 may control the rotating speed, the number of revolution, etc. of each of the first driving motor 320a and the second driving motor 320b such that the first rotating shaft 310a and the second rotating shaft 310b rotate alternatively, thereby inducing the sawing of the wire saw 201. In addition, the controller 330 may suitably change the rotating speed, the number of revolution, etc. of the driving motor 320 based on a state or size of the tibia T.

Referring to a method of use of the semi-cylindrical osteotomy device 10, a side surface of the tibia T is exposed, and then the anterior guide pipe 111 and the posterior guide pipe 112 are rotated based on the hinge 131 to be inserted respectively into the anterior portion and the posterior portion of the tibia T. In other words, the anterior guide pipe 111 and the posterior guide pipe 112 are respectively inserted into the anterior portion and the posterior portion of the tibia T to arrange the guide portion 100 along the outer circumference of the tibia T. At this time, the connecting unit 130 may stably support the anterior guide pipe 111 and the posterior guide pipe 112 from the side surface of the tibia T. The wire saw 201 is inserted along the internal spaces 102 of the inserted anterior guide pipe 111 and posterior guide pipe 112, and then the both ends of the wire saw 201 are connected to the driving unit 300. In other words, the one end of the wire saw 201 is connected to the first rotating shaft 310a and the other end of the wire saw 201 is connected to the second rotating shaft 310b. The driving unit 300 winds the both ends of the wire saw 201 to move the wire saw 201 from the other ends to the one ends of the anterior guide pipe 111 and posterior guide pipe 112. In other words, the wire saw 201 may cut the tibia T in the curved surface by being wound to traverse the tibia accommodating space 101 along the anterior slit 121 and the posterior slit 122.

Figure 6:
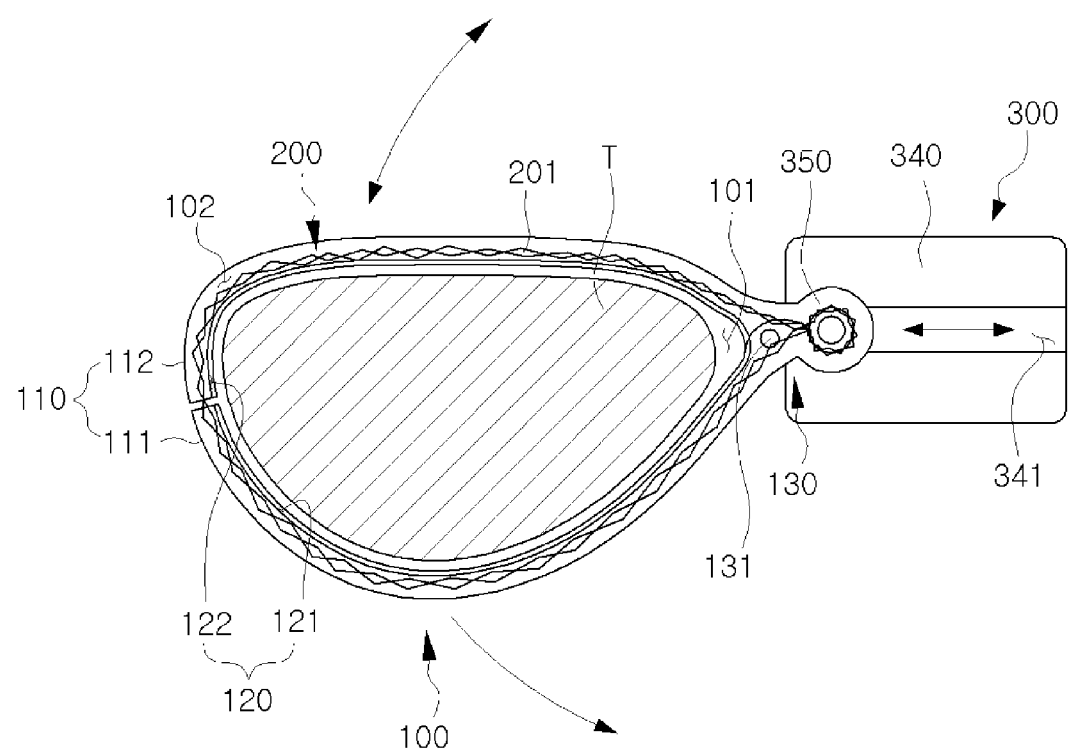
FIG. 6 is a cross-sectional view of the semi-cylindrical osteotomy device of FIG. 2 cut along the guide portion to show another embodiment of a driving unit.

Meanwhile, FIG. 6 is a cross-sectional view illustrating a second embodiment of the driving unit 300 of the present disclosure. Referring to the second embodiment of the driving unit 300 with reference to FIG. 6, the driving unit 300 includes a body 340 and a moving body 350.

The body 340 is provided at one side of the guide portion 100 and includes a space therein. One end of the body 340 may be opened such that the inside of the body 340 communicates with the connecting unit 130. Also, a guide groove 341 may be formed inside the body 340. The moving body 350 described below may move along the guide groove 341.

The both ends of the wire saw 201 is fixed to the moving body 350, and the moving body 350 slidably moves by being provided inside the body 340. In other words, the moving body 350 may be arranged in the guide groove 341 to move along the guide groove 341. When the moving body 350 slidably moves along the body 340, the wire saw 201 is moved from the other ends to the one ends of the anterior guide pipe 111 and posterior guide pipe 112 and cuts the tibia T. In other words, the movable body 350 may slidably move while alternately rotating in both directions, thereby inducing sawing.

Meanwhile, the driving unit 300 is not limited to causing rotation of the rotating shaft 310 and slidable movement of the moving body 350, but may cause the driving motor 320 and the moving body 350 to be manually operated or cause the moving body 350 to move a space of the body 340 via a slider motor, a cylinder, or the like. In addition, the driving unit 300 may be formed such that an outer side is holdable, and thus may be used as a handle.

In the present disclosure, the semi-cylindrical osteotomy device 10 is described as a device for cutting the tibia T, but may be applicable to a region other than the tibia T, which need to be cut in a semi-cylindrical shape.

According to the semi-cylindrical osteotomy device 10 according to the present disclosure, stability of a surgery is increased by inserting the guide portion 100 by approaching the side surface of the tibia T to minimize an exposed portion of a bone.

Also, the wire saw 201 moves along the slit 120 of the guide portion 100, and thus a cut bone surface of a semi-cylindrical shape may be easily and quickly formed.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

EXPLANATION OF REFERENCE NUMERALS

| 10: | Semi-cylindrical osteotomy device | 100: | Guide portion |
|---|---|---|---|
| 101: | Tibia accommodating space | 102: | Internal space |
| 110: | Pipe | 111: | Anterior guide pipe |
| 112: | Posterior guide pipe | 120: | Slit |
| 121: | Anterior slit | 122: | Posterior slit |
| 130: | Connecting unit | 131: | Hinge |
| 200: | Cutter portion | 201: | Wire saw |
| 300: | Driving unit | 310: | Rotating shaft |

| | | | |
|---|---|---|---|
| 310a: | First rotating shaft | 310b: | Second rotating shaft |
| 320: | Driving motor | 320a: | First driving motor |
| 320b: | Second driving motor | 330: | Controller |
| 340: | Body | 341: | Guide groove |
| 350: | Moving body | T: | Tibia |

The invention claimed is:

1. A semi-cylindrical osteotomy device comprising:
 a guide portion defining a space in which a tibia is accommodated;
 a cutter portion moving along an inner circumferential surface of the guide portion to cut the tibia; and
 a driving unit driving the cutter portion and comprising:
  a rotating shaft in the form of a movable body around which both ends of the cutter portion are fixed and wound;
  a driving motor controlling the rotating shaft; and
  a controller controlling the driving motor.

2. The semi-cylindrical osteotomy device of claim 1, wherein the guide portion includes a center curved portion.

3. The semi-cylindrical osteotomy device of claim 2, wherein the guide portion comprises:
 a hollow pipe to accommodate the cutter portion, wherein the hollow pipe is configured to be arranged along an outer circumference of the tibia; and
 a slit formed along an inner circumference defined by the hollow pipe.

4. The semi-cylindrical osteotomy device of claim 3, wherein the cutter portion is configured as a wire saw arranged configured to be along the outer circumference of the tibia and wherein the wire saw cuts the tibia in a circumferential direction by moving through the slit.

5. The semi-cylindrical osteotomy device of claim 4, wherein the driving unit further comprises:
 a body located at one side of the guide portion and having a channel formed inside the body; wherein the movable body slidably and rotatably moves inside the channel.

6. The semi-cylindrical osteotomy device of claim 3, wherein the hollow pipe comprises:
 an anterior guide pipe portion configured to be arranged along an anterior portion of the tibia, including a center portion having a semi-circular shape, and including an anterior slit along a length thereof, along a side configured to contact the tibia;
 a posterior guide pipe portion configured to be arranged along a posterior portion of the tibia, including a center portion having a semi-circular shape, and including a posterior slit along a length thereof, along a side configured to contact the tibia; and
 a connecting unit provided at one end of the anterior guide pipe portion and at one end of the posterior guide pipe portion, thereby connecting the anterior guide pipe portion and the posterior guide pipe portion.

7. The semi-cylindrical osteotomy device of claim 6, wherein the cutter portion is configured as a wire saw, provided in an inner space of the anterior guide pipe portion and an inner space of the posterior guide pipe portion, and cuts the tibia in a circumferential direction by moving through and along the anterior slit and the posterior slit.

8. The semi-cylindrical osteotomy device of claim 1, wherein the cutter portion moves along the inner circumferential surface of the guide portion and cuts the tibia in a circumferential direction.

\* \* \* \* \*